(12) United States Patent
Shimizukawa et al.

(10) Patent No.: US 10,838,079 B2
(45) Date of Patent: Nov. 17, 2020

(54) RADIOGRAPHIC IMAGE DETECTION DEVICE

(71) Applicant: FUJIFILM Corporation, Tokyo (JP)

(72) Inventors: Sho Shimizukawa, Ashigarakami-gun (JP); Hiroki Koketsu, Ashigarakami-gun (JP); Koji Taninai, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 64 days.

(21) Appl. No.: 16/292,653

(22) Filed: Mar. 5, 2019

(65) Prior Publication Data
US 2019/0277979 A1    Sep. 12, 2019

(30) Foreign Application Priority Data

Mar. 6, 2018 (JP) ................. 2018-039373

(51) Int. Cl.
| | |
|---|---|
| *G01T 1/17* | (2006.01) |
| *A61B 6/00* | (2006.01) |
| *G01T 1/175* | (2006.01) |
| *G01N 23/04* | (2018.01) |

(52) U.S. Cl.
CPC .............. *G01T 1/17* (2013.01); *A61B 6/4233* (2013.01); *A61B 6/4283* (2013.01); *A61B 6/505* (2013.01); *A61B 6/54* (2013.01); *A61B 6/542* (2013.01); *A61B 6/56* (2013.01); *G01N 23/04* (2013.01); *G01T 1/175* (2013.01)

(58) Field of Classification Search
CPC ..... A61B 6/4233; A61B 6/4283; A61B 6/505; A61B 6/54; A61B 6/542; A61B 6/56; G01N 23/04; G01T 1/17; G01T 1/175
See application file for complete search history.

(56) References Cited

U.S. PATENT DOCUMENTS

2018/0031715 A1    2/2018 Kuwabara

FOREIGN PATENT DOCUMENTS

JP    2018-015455 A    2/2018

*Primary Examiner* — Mark R Gaworecki
(74) *Attorney, Agent, or Firm* — Birch, Stewart, Kolasch & Birch, LLP

(57) ABSTRACT

A first power supply unit supplies power to a first sensor panel and a first circuit unit. A second power supply unit supplies power to a second sensor panel and a second circuit unit. A synchronizing signal supply unit of a control unit supplies a synchronizing signal for synchronizing the operations of a switching power supply of the first power supply unit and a switching power supply of the second power supply unit to the switching power supply of the first power supply unit and the switching power supply of the second power supply unit. Since the operations of the first and second power supply units are the same in each imaging operation, it is possible to ensure the reproducibility of an X-ray image.

6 Claims, 8 Drawing Sheets

RADIOGRAPHIC IMAGE DETECTION DEVICE

CROSS-REFERENCE TO RELATED APPLICATIONS

This application claims priority under 35 U.S.C § 119(a) to Japanese Patent Application No. 2018-039373 filed on 6 Mar. 2018. The above application is hereby expressly incorporated by reference, in its entirety, into the present application.

BACKGROUND OF THE INVENTION

1. Field of the Invention

The present invention relates to a radiographic image detection device.

2. Description of the Related Art

In a medical field, a diagnosis is made on the basis of a radiographic image detected by a radiographic image detection device. The radiographic image detection device comprises a sensor panel, a circuit unit, and a power supply unit. In the sensor panel, a plurality of pixels that accumulate charge in response to radiation which has been emitted from a radiation source and then transmitted through a subject (patient) are two-dimensionally arranged. The radiographic image detection device comprising the sensor panel is also called a flat panel detector (FPD). The circuit unit converts the charge accumulated in the pixels of the sensor panel into a digital signal and outputs the digital signal as a radiographic image. The power supply unit supplies power to the sensor panel and the circuit unit. The power supply unit is provided with a switching power supply that outputs a desired voltage using a pulse modulation method, for example, a pulse width modulation (hereinafter, abbreviated to PWM) method.

As disclosed in JP2018-015455A (corresponding to US2018/031715A1), a radiographic image detection device comprises a plurality of sensor panels. The radiographic image detection device disclosed in JP2018-015455A is used for a so-called energy subtraction (hereinafter, abbreviated to ES) method. Specifically, the radiographic image detection device disclosed in JP2018-015455A has a configuration in which two sensor panels are sequentially arranged in a thickness direction and charge is accumulated in the pixels of two sensor panels at the same time by one radiation emission operation. Then, a bone tissue image and/or a soft tissue image except bone tissues is generated or an index value related to bones, such as a bone mass or bone density, is calculated, on the basis of two radiographic images detected by two sensor panels.

In JP2018-015455A, two circuit units are provided for each sensor panel. In addition, in JP2018-015455A, one power supply unit supplies power to each sensor panel and each circuit unit. However, in practice, two power supply units are provided for each pair of the sensor panel and the circuit unit.

SUMMARY OF THE INVENTION

In the radiographic image detection device comprising a plurality of sensor panels as in JP2018-015455A, noise is generated by the interaction of each circuit unit and each power supply unit and artifacts are generated in a radiographic image due to the noise.

In a case in which the noise caused by the interaction of each circuit unit and each power supply unit is different in each imaging operation, artifacts generated in the radiographic image are different in each imaging operation. Therefore, even in a case in which the image of the same subject is captured under exactly the same conditions, a radiographic image in which artifacts are not constant is obtained since the influence of artifacts is different in each imaging operation, which makes it difficult to obtain the same radiographic image in each imaging operation. That is, it is difficult to ensure the reproducibility of a radiographic image. The problem that it is difficult to ensure the reproducibility of the radiographic image is an important problem to be solved especially since the reliability of the index value is significantly reduced in a system for calculating the index value related to bones as in JP2018-015455A.

An object of the invention is to provide a radiographic image detection device that can ensure the reproducibility of a radiographic image.

In order to solve the above-mentioned problems, according to the invention, there is provided a radiographic image detection device comprising: a plurality of sensor panels in which pixels that accumulate charge in response to radiation, which has been emitted from a radiation source and transmitted through a subject, are two-dimensionally arranged; a plurality of circuit units each of which is provided in each of the plurality of sensor panels, converts the charge into a digital signal, and outputs the digital signal as a radiographic image; a plurality of power supply units each of which is provided for each pair of the sensor panel and the circuit unit and supplies power to each pair of the sensor panel and the circuit unit; and a synchronizing signal supply unit that supplies a synchronizing signal for synchronizing operations of the plurality of power supply units to the plurality of power supply units.

Preferably, the radiographic image detection device further comprises a control unit that controls operations of the sensor panels. Preferably, the synchronizing signal supply unit is provided in the control unit. Alternatively, it is preferable that the synchronizing signal supply unit is provided in one of the plurality of power supply units.

Preferably, the synchronizing signal is used as a clock signal for regulating operations of the circuit units.

Preferably, the plurality of sensor panels are sequentially arranged in a thickness direction.

Preferably, a plurality of the radiographic images output from the plurality of circuit units are used to calculate an index value related to bones.

According to the invention, the synchronizing signal for synchronizing the operations of a plurality of power supply units each of which supplies power to each of a plurality of pairs of the sensor panels and the circuit units is supplied to the plurality of power supply units. Therefore, noise caused by the interaction of each circuit unit and each power supply unit is always the same in each imaging operation and artifacts generated in the radiographic image are always the same in each imaging operation. As a result, it is possible to provide a radiographic image detection device that can ensure the reproducibility of a radiographic image.

DESCRIPTION OF THE PREFERRED EMBODIMENTS

First Embodiment

Figure 1:
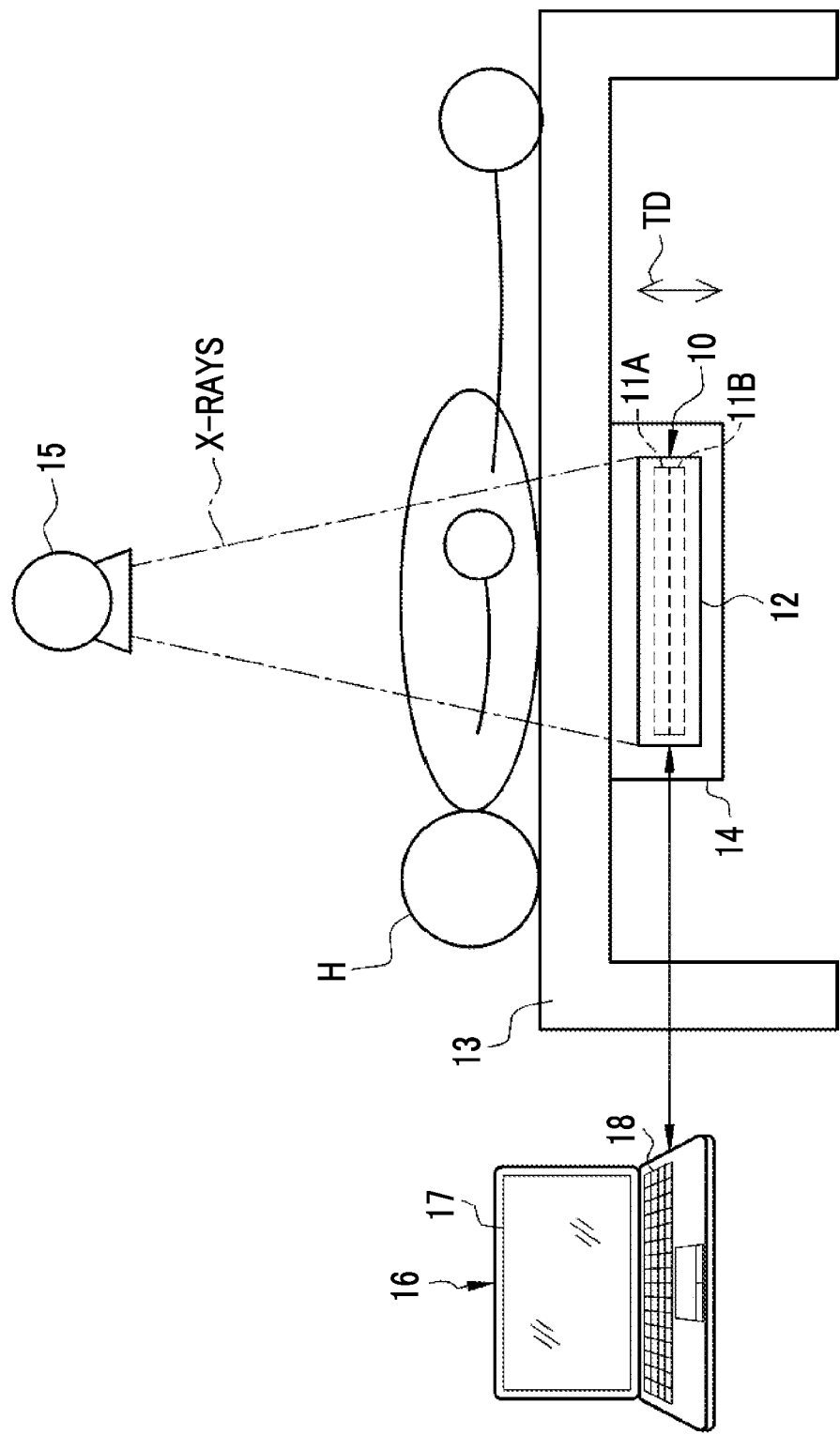
FIG. 1 is a diagram illustrating an aspect of X-ray imaging.

In FIG. 1, an electronic cassette 10 corresponding to a radiographic image detection device according to the invention has a first sensor panel 11A and a second sensor panel 11B which are accommodated in a housing 12. The first and second sensor panels 11A and 11B are thin plates having a rectangular shape in a plan view and are sequentially arranged in a thickness direction TD.

The housing 12 is a portable box having a rectangular parallelepiped shape and has a size which is based on the International Organization for Standardization (ISO) 4090: 2001 and is substantially equal to the size of, for example, a film cassette, an imaging plate (IP) cassette, or a computed radiography (CR) cassette. The housing 12 is made of a conductive material, such as a resin mixed with carbon fibers, a resin mixed with an aluminum or nickel filler, an aluminum alloy, or a magnesium alloy.

The electronic cassette 10 is set in a holder 14 of an imaging table 13 on which a subject H lies supine. Then, the electronic cassette 10 receives X-rays (represented by a one-dot chain line) corresponding to radiation which has been emitted from an X-ray source 15 corresponding to a radiation source and then transmitted through the subject H and detects an X-ray image corresponding to a radiographic image.

The electronic cassette 10 is connected to a console 16 and communicates with the console 16 to transmit and receive various kinds of information. Various kinds of information include, for example, the X-ray images detected by the electronic cassette 10 and an imaging menu input by an operator through the console 16. The imaging menu is, for example, a set of an imaging part, such as the head or the chest, a posture, such as an upright position, a lying position, or a sitting position, and the orientation of the subject H with respect to X-rays, such as the front, the side, or the back.

For example, the console 16 is configured by installing a control program, such as an operating system, and various application programs in a computer such as a notebook personal computer. The console 16 includes a display 17 and an input device 18 such as a touch pad or a keyboard. For example, the X-ray image transmitted from the electronic cassette 10 is displayed on the display 17.

Figure 2:
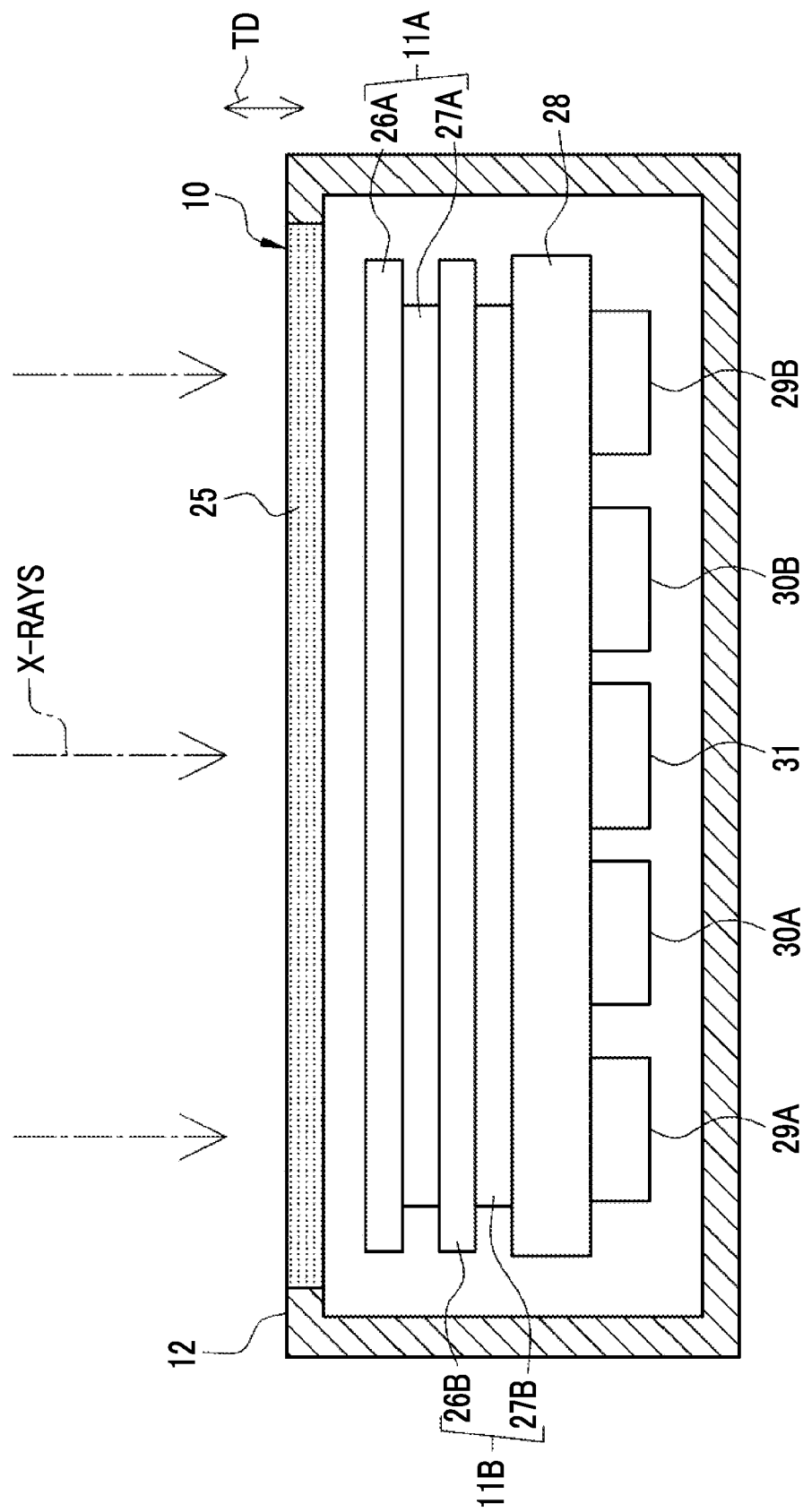
FIG. 2 is a diagram illustrating the internal structure of an electronic cassette.

In FIG. 2, a rectangular opening is formed in a front surface of the housing 12 on which X-rays are incident and a transmission plate 25 that transmits X-rays is attached to the opening. The first sensor panel 11A and the second sensor panel 11B are provided immediately below the transmission plate 25. Here, the thickness direction TD in which the first and second sensor panels 11A and 11B are sequentially arranged is a direction that is parallel to a line normal to the front surface of the housing 12 and a rear surface of the housing 12 opposite to the front surface. The first sensor panel 11A includes a first light detection substrate 26A and a first scintillator 27A. The first light detection substrate 26A and the first scintillator 27A are arranged in the order of the first light detection substrate 26A and the first scintillator 27A as viewed from the front surface of the housing 12 on which X-rays are incident. Similarly, the second sensor panel 11B includes a second light detection substrate 26B and a second scintillator 27B which are arranged in the order of the second light detection substrate 26B and the second scintillator 27B as viewed from the front surface of the housing 12. In addition, a sensor panel in which a scintillator 27 and a light detection substrate 26 are sequentially arranged as viewed from the front surface of the housing 12 may be used. Further, a direct-conversion-type sensor panel that directly converts X-rays into charge with a photoconductive film made of, for example, amorphous selenium may be used.

The first scintillator 27A has a phosphor, such as CsI:Tl (thallium-activated cesium iodide), and the second scintillator 27B has a phosphor, such as GOS ($Gd_2O_2S$:Tb, terbium-activated gadolinium oxysulfide). Each of the first and second scintillators 27A and 27B converts incident X-rays into visible light and emits the visible light. The first and second light detection substrates 26A and 26B detect the visible light emitted from the first and second scintillators 27A and 27B and convert the visible light into charge.

The housing 12 accommodates a base 28, a first circuit unit 29A, a second circuit unit 29B, a first power supply unit 30A, a second power supply unit 30B, and a control unit 31 in addition to the first and second sensor panels 11A and 11B. The first and second sensor panels 11A and 11B are attached to a front surface (on which X-rays are incident) of the base 28 and the first and second circuit units 29A and 29B, the first and second power supply units 30A and 30B, and the control unit 31 are attached to a rear surface (opposite to the front surface) of the base 28. The base 28 is fixed to the inner surface of the housing 12 by, for example, a resin adhesive. Further, the housing 12 accommodates a cable connector (not illustrated) that performs wired communication with the console 16 and receives power from a commercial power supply in addition to these components. The housing 12 may accommodate an antenna for wireless communication with the console 16 and a battery for wirelessly driving the electronic cassette 10.

Each of the first and second circuit units 29A and 29B, the first and second power supply units 30A and 30B, and the control unit 31 is electrically connected to the housing 12 through the base 28 and has a ground potential. That is, the first and second circuit units 29A and 29B, the first and second power supply units 30A and 30B, and the control unit 31 share a ground return path.

The first circuit unit 29A is for the first sensor panel 11A and the first power supply unit 30A is for the first sensor panel 11A and the first circuit unit 29A. In addition, the second circuit unit 29B is for the second sensor panel 11B and the second power supply unit 30B is for the second sensor panel 11B and the second circuit unit 29B. That is, the first circuit unit 29A is provided for the first sensor panel 11A and the second circuit unit 29B is provided for the second sensor panel 11B. The first power supply unit 30A is provided for a pair of the first sensor panel 11A and the first circuit unit 29A and the second power supply unit 30B is provided for a pair of the second sensor panel 11B and the second circuit unit 29B.

Figure 3:
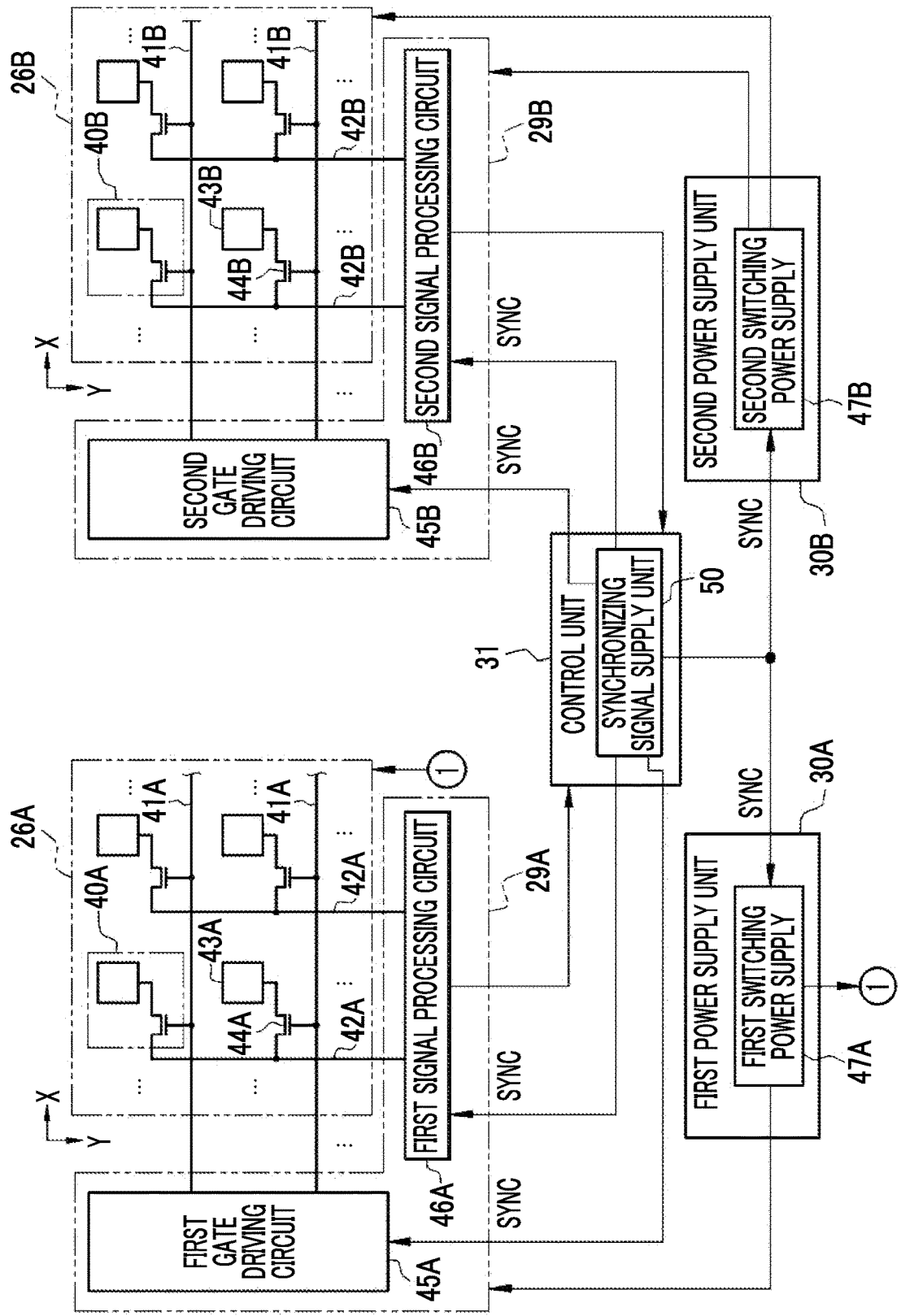
FIG. 3 is a block diagram illustrating the electrical configuration of the electronic cassette.

In FIG. 3, the first light detection substrate 26A is configured by providing first pixels 40A which are arranged in a two-dimensional matrix of N rows and M columns, N first gate lines 41A, and M first signal lines 42A on a glass substrate (not illustrated). The first gate lines 41A extend in the X direction along a row direction of the first pixels 40A and are arranged at a predetermined pitch in the Y direction along a column direction of the first pixels 40A. The first signal lines 42A extend in the Y direction and are arranged at a predetermined pitch in the X direction. The first gate lines 41A and the first signal lines 42A are orthogonal to each other and the first pixels 40A are provided so as to correspond to the intersection points between the first gate lines 41A and the first signal lines 42A.

N and M are integers that are equal to or greater than 2. For example, N is 2880 and M is 2304. In addition, the array of the first pixels 40A may be a square array as illustrated in FIG. 3. The first pixels 40A may be inclined at 45° and may be arranged in zigzag.

As is well known, the first pixel 40A comprises a first photoelectric conversion unit 43A on which visible light is incident and which generates charge (electron-hole pair) and accumulates the charge and a first thin film transistor (TFT) 44A. The first photoelectric conversion unit 43A has a structure in which an upper electrode and a lower electrode are provided on the upper and lower sides of a semiconductor layer that generates charge. The semiconductor layer is, for example, a p-intrinsic-n (PIN) type and includes an N-type layer provided on the upper electrode side and a P-type layer provided on the lower electrode side. The first TFT 44A has a gate electrode connected to the first gate line 41A, a source electrode connected to the first signal line 42A, and a drain electrode connected to the lower electrode of the first photoelectric conversion unit 43A. In addition, a light detection substrate that is not a TFT type, but is a complementary metal oxide semiconductor (CMOS) type may be used.

A bias line (not illustrated) is connected to the upper electrode of the first photoelectric conversion unit 43A. A positive bias voltage is applied to the upper electrode through the bias line. The positive bias voltage is applied to generate an electric field in the semiconductor layer. Therefore, in the electron-hole pair generated in the semiconductor layer by photoelectric conversion, the electron is moved to the upper electrode and is absorbed by the bias line and the hole is moved to the lower electrode and is collected as charge.

The second light detection substrate 26B has the same configuration as the first light detection substrate 26A. Therefore, alphabet "B" is added next to numbers for components of the second light detection substrate 26B to distinguish the components from the components of the first light detection substrate 26A and the description of the components will not be repeated.

The first circuit unit 29A includes a first gate driving circuit 45A and a first signal processing circuit 46A. The first gate driving circuit 45A is connected to the ends of the first gate lines 41A and generates a gate pulse for driving the first TFTs 44A. The control unit 31 drives the first TFTs 44A through the first gate driving circuit 45A and controls the driving of the first signal processing circuit 46A to control the operation of the first sensor panel 11A. Specifically, the control unit 31 directs the first sensor panel 11A to perform a pixel reset operation which reads dark charge from the first pixel 40A and resets (removes) the dark charge, a pixel charge accumulation operation which accumulates charge corresponding to the amount of X-rays reaching the first pixel 40A in the first pixel 40A, and an image reading operation which reads the charge accumulated in the first pixel 40A to the first signal processing circuit 46A through the first signal line 42A.

The first signal processing circuit 46A converts the accumulated charge read from the first pixel 40A by the image reading operation into an analog voltage signal. Then, the first signal processing circuit 46A performs a known correlated double sampling process for the analog voltage signal to remove a noise component from the analog voltage signal. Then, the first signal processing circuit 46A converts the analog voltage signal into a digital signal corresponding to the voltage value of the analog voltage signal (analog/digital conversion) and outputs the digital signal to the control unit 31. The control unit 31 stores the digital signal output from the first signal processing circuit 46A as an X-ray image (a first X-ray image, see FIG. 6) in an embedded memory (not illustrated). In addition, the second circuit unit 29B has the same configuration as the first circuit unit 29A. Therefore, similarly to the second light detection substrate 26B, alphabet "B" is added next to numbers for components of the second circuit unit 29B to distinguish the components from the components of the first circuit unit 29A and the description of the components will not be repeated.

The first power supply unit 30A supplies power to the first sensor panel 11A and the first circuit unit 29A under the control of the control unit 31. Similarly, the second power supply unit 30B supplies power to the second sensor panel 11B and the second circuit unit 29B under the control of the control unit 31.

The first power supply unit 30A is provided with a first switching power supply 47A and the second power supply unit 30B is provided with a second switching power supply 47B. The switching power supplies 47A and 47B convert a voltage based on power from a battery or a commercial power supply into a voltage suitable for the first and second sensor panels 11A and 11B and the first and second circuit units 29A and 29B using, for example, a PWM method and output the voltage (see FIGS. 4 and 5).

The control unit 31 is provided with a synchronizing signal supply unit 50. The synchronizing signal supply unit 50 supplies a synchronizing signal SYNC to the first and second switching power supplies 47A and 47B of the first and second power supply units 30A and 30B. The synchronizing signal SYNC is a signal for synchronizing the operations of the first and second power supply units 30A and 30B.

Figure 4:
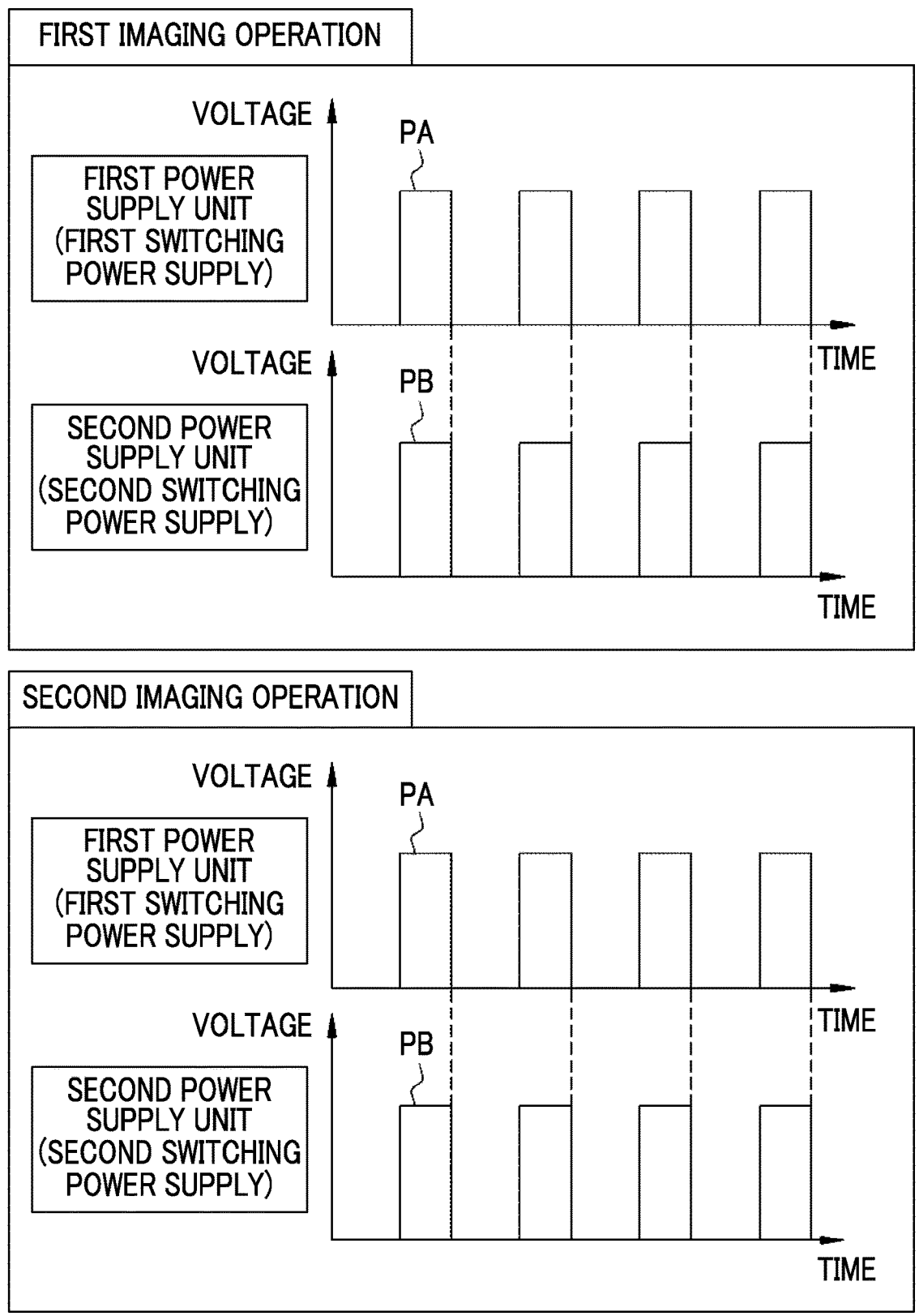
FIG. 4 is a diagram illustrating an example in which the operation of each power supply unit is synchronized and illustrates a case in which the phases of the pulses of each switching power supply of each power supply unit are aligned with each other.
Figure 5:
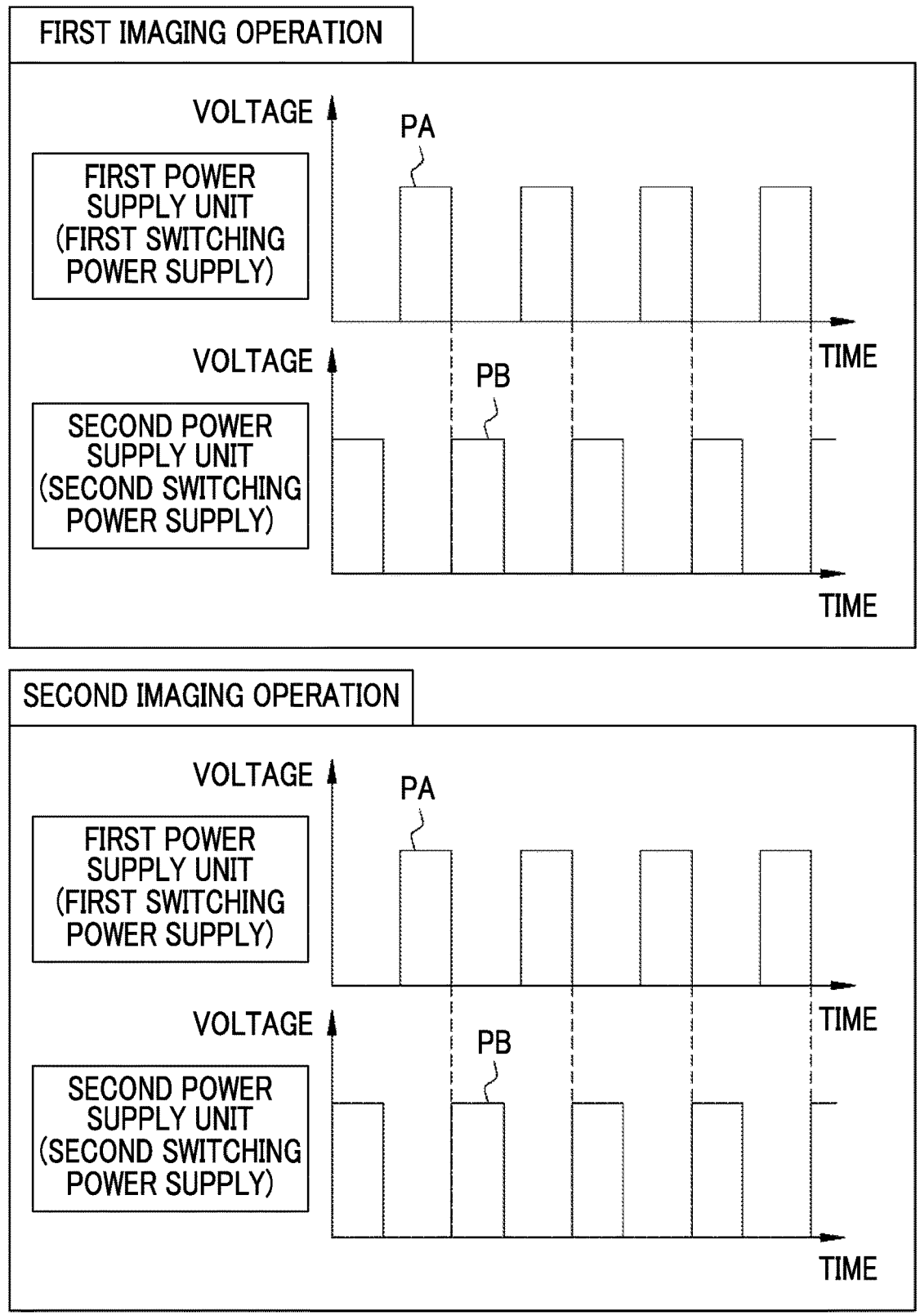
FIG. 5 is a diagram illustrating an example in which the operation of each power supply unit is synchronized and illustrates a case in which the phases of the pulses of each switching power supply of each power supply unit deviate from each other.

Here, the term "synchronizing the operations of the first and second power supply units 30A and 30B" means causing the first and second power supply units 30A and 30B to perform the same operation in each imaging operation as illustrated in FIGS. 4 and 5. In other words, the term "synchronizing the operations of the first and second power supply units 30A and 30B" means causing the first and second switching power supplies 47A and 47B to output pulses PA and PB at the same time in each imaging operation.

FIG. 4 illustrates a case in which the phases of the pulses PA and PB are aligned with each other. FIG. 5 illustrates a case in which the phases of the pulses PA and PB deviate from each other. As such, for example, in a case in which the phases of the pulses PA and PB deviate from each other and the amount of deviation is the same in each imaging operation, it can be said that the operations of the first and second power supply units 30A and 30B are the same in each imaging operation.

Returning to FIG. 3, the synchronizing signal supply unit 50 supplies the synchronizing signal SYNC to the first and second gate driving circuits 45A and 45B and the first and second signal processing circuits 46A and 46B of the first and second circuit units 29A and 29B in addition to the first and second switching power supplies 47A and 47B of the first and second power supply units 30A and 30B. Each of the first and second gate driving circuits 45A and 45B generates a gate pulse at a timing corresponding to the synchronizing signal SYNC. Each of the first and second signal processing circuits 46A and 46B performs, for example, the output of an analog voltage signal, correlated double sampling, and analog/digital conversion at the timing corresponding to the synchronizing signal SYNC. That is, the synchronizing signal SYNC is also used as a clock signal for regulating the operations of the first and second circuit units 29A and 29B.

Figure 6:
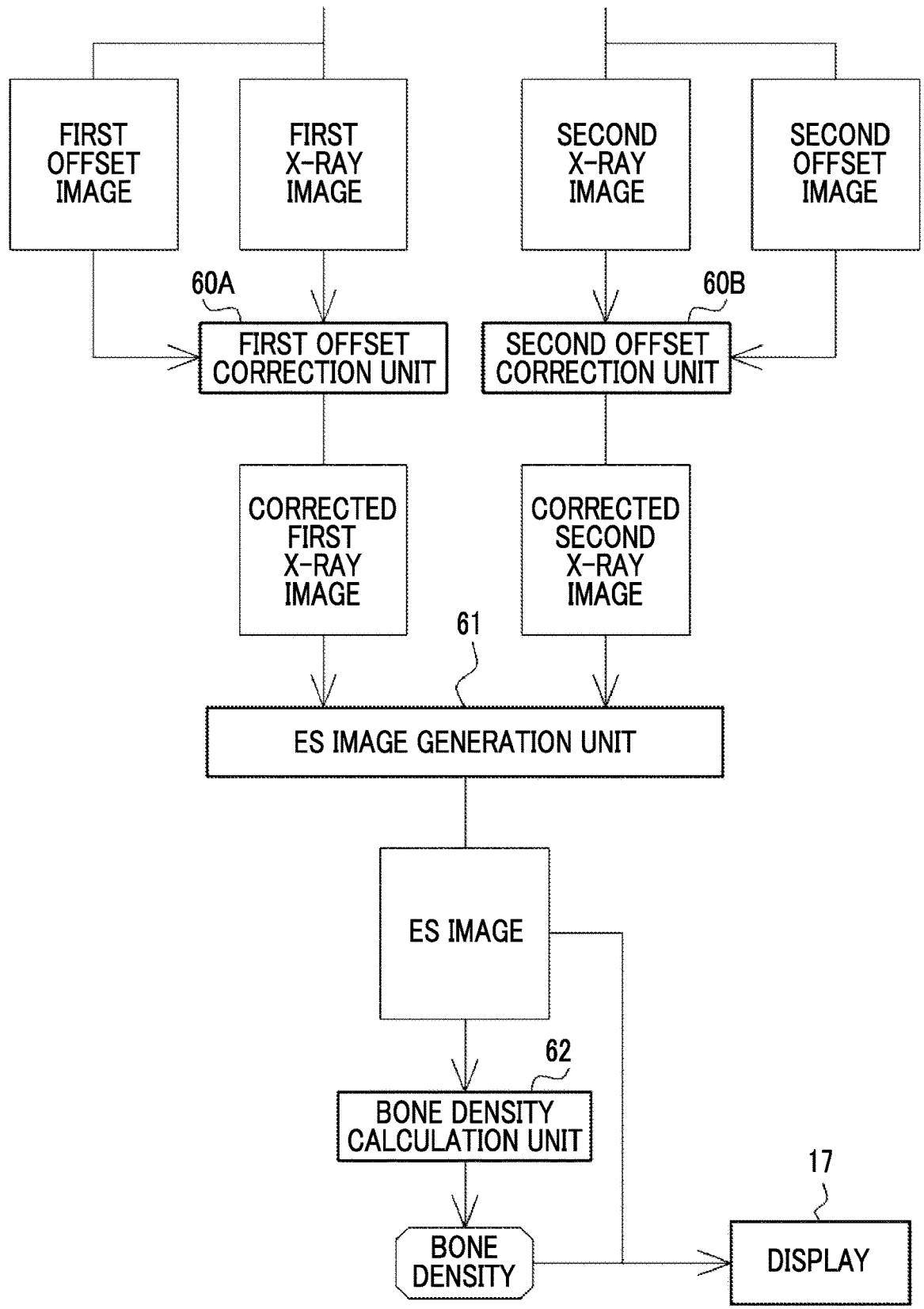
FIG. 6 is a block diagram illustrating the configuration of a console related to the calculation of bone density.

In FIG. 6, the console 16 receives a first X-ray image and a first offset image from the first sensor panel 11A and receives a second X-ray image and a second offset image from the second sensor panel 11B. The first X-ray image and the second X-ray image are based on the charge accumulated in the first and second pixels 40A and 40B in response to the X-rays which have been emitted from the X-ray source 15 and then transmitted through the subject H, respectively, and indicate the internal structure of the body of the subject H. In contrast, the first offset image and the second offset image are obtained by performing an image reading operation for the first sensor panel 11A and the second sensor panel 11B in a state in which no X-rays are emitted and have fixed pattern noise mixed therewith. Each offset image is acquired, for example, in a case in which the electronic cassette 10 is turned on at the time of starting the medical facility. Of course, each offset image may be acquired whenever each imaging operation is performed.

As described above, the first and second circuit units 29A and 29B, the first and second power supply units 30A and 30B, and the control unit 31 share the ground return path. Therefore, a return current flows from one of the first and second circuit units 29A and 29B to the other circuit unit through the ground return path, which results in a variation in ground potential. Noise caused by the variation in ground potential is noise caused by the interaction of the first and second circuit units 29A and 29B and the first and second power supply units 30A and 30B and includes the fixed pattern noise mixed with each offset image. Another example of the fixed pattern noise is noise caused by the usage environment of the electronic cassette 10 such as environmental temperature.

A first offset correction unit 60A subtracts the first offset image from the first X-ray image in units of pixels. Then, artifacts caused by the fixed pattern noise are removed from the first X-ray image and a corrected first X-ray image is obtained. Similarly, a second offset correction unit 60B subtracts the second offset image from the second X-ray image in units of pixels. Then, artifacts caused by the fixed pattern noise are removed from the second X-ray image and a corrected second X-ray image is obtained.

An ES image generation unit 61 generates an ES image from the corrected first X-ray image from the first offset correction unit 60A and the corrected second X-ray image from the second offset correction unit 60B. Specifically, the ES image generation unit 61 subtracts an image obtained by multiplying the corrected first X-ray image by a predetermined coefficient from an image obtained by multiplying the corrected second X-ray image by a predetermined coefficient in units of pixels. The ES image generated by the subtraction process is, for example, an image in which soft tissues have been removed and bone tissues have been highlighted.

A bone density calculation unit 62 calculates bone density in an imaging part of the subject H as an index value related to bones. Specifically, first, the bone density calculation unit 62 analyzes the ES image from the ES image generation unit 61 to extract a bone tissue region of the ES image. Then, for example, the bone density calculation unit 62 multiplies a representative value (for example, the mean, maximum value, or mode) of the pixel values of the bone tissue region by a conversion coefficient for converting the pixel values into a bone mass to calculate the bone mass. The bone density calculation unit 62 divides the calculated bone mass by the area of the bone tissue region to calculate bone density.

The console 16 displays, for example, the bone density calculated by the bone density calculation unit 62 and the ES image generated by the ES image generation unit 61 on the display 17. As such, the X-ray images output from the first and second sensor panels 11A and 11B are used to calculate the index value related to bones. Further, in addition to or instead of the bone density, the bone mass may be displayed on the display 17.

For example, an application program related to X-ray imaging is executed to construct the first and second offset correction units 60A and 60B, the ES image generation unit 61, and the bone density calculation unit 62 in a central processing unit (CPU) of the console 16. Some or all of the above-mentioned units may be constructed in the CPU of the electronic cassette 10 and the electronic cassette 10 may perform offset correction or bone density calculation.

Next, the operation of the above-mentioned configuration will be described. In a case in which X-ray imaging is performed for the subject H using the electronic cassette 10, the operator turns on the electronic cassette 10 and sets the electronic cassette 10 in the holder 14 of the imaging table 13. Then, the operator adjusts the positional relationship among the electronic cassette 10, the X-ray source 15, and the subject H and then operates the X-ray source 15 to emit X-rays.

The X-rays which have been emitted from the X-ray source 15 and then transmitted through the subject H are incident on the first sensor panel 11A and the second sensor panel 11B through the transmission plate 25. Each of the first and second sensor panels 11A and 11B receive the emitted X-rays and sequentially perform the pixel reset operation and the pixel charge accumulation operation. The charge corresponding to the amount of X-rays reaching each of the first and second pixels 40A and 40B is accumulated in each of the first and second pixels 40A and 40B.

After the emission of the X-rays ends, the image reading operation is performed in each of the first and second sensor panels 11A and 11B. Then, the first X-ray image and the second X-ray image are output from the first sensor panel 11A and the second sensor panel 11B, respectively.

As illustrated in FIG. 3, in the electronic cassette 10, the synchronizing signal supply unit 50 supplies the synchronizing signal SYNC to the first and second switching power supplies 47A and 47B of the first and second power supply units 30A and 30B. As illustrated in FIGS. 4 and 5, the operations of the first and second power supply units 30A and 30B are synchronized by the synchronizing signal SYNC. As a result, the operations of the first and second power supply units 30A and 30B are the same in each imaging operation.

Since the operations of the first and second power supply units 30A and 30B are the same in each imaging operation, noise caused by a variation in ground potential is always the same in each imaging operation. It is possible to suppress the amount of variation in artifacts generated in the X-ray image due to noise caused by at least a variation in ground potential to a desired range. Therefore, it is possible to ensure the reproducibility of the X-ray image. In addition, the desired range of the amount of variation in artifacts is, for example, $1\sigma=2$ LSB (least significant bit) in absolute value, which has been derived from a variation coefficient of a reproducibility test based on the Japanese Industrial Standards (JIS) standard Z4930 (performance evaluation of X-ray bone densitometer).

As illustrated in FIG. 3, the synchronizing signal supply unit 50 is provided in the control unit 31 and the synchronizing signal SYNC is also supplied to the first and second gate driving circuits 45A and 45B and the first and second signal processing circuits 46A and 46B of the first and second circuit units 29A and 29B. Therefore, the synchronizing signal SYNC can be effectively used not only to synchronize the operations of the first and second power supply units 30A and 30B, but also to regulate the operations of the first and second circuit units 29A and 29B.

Each X-ray image is transmitted from the electronic cassette 10 to the console 16. In the console 16, as illustrated in FIG. 6, each of the first and second offset correction units 60A and 60B removes the artifacts caused by the fixed pattern noise from each X-ray image. At that time, artifacts generated due to noise caused by a variation in ground potential which is noise caused by the interaction of the first and second circuit units 29A and 29B and the first and second power supply units 30A and 30B are also suppressed.

In a case in which the operations of the first and second power supply units 30A and 30B are not synchronized with each other and the noise caused by a variation in ground potential is different in each imaging operation, the amount of artifacts removed by each of the first and second offset correction units 60A and 60B (the amount of noise caused by a variation in ground potential in each offset image) is different from that at the time of capturing each X-ray image. As a result, it is difficult to ensure the reproducibility of the X-ray image. For example, in a case in which the amount of noise caused by a variation in ground potential in the first offset image is 10 and the amount of noise caused by a variation in ground potential in the first X-ray image is 8, excessive offset correction has been performed. In contrast, in the invention, since the operations of the first and second power supply units 30A and 30B are synchronized with each other, the above-mentioned problem does not occur. In addition, the ensuring of the reproducibility of the X-ray image is synonymous with suppressing the amount of variation in artifacts which are superimposed on the X-ray image due to the noise caused by a variation in ground potential to a desired range.

After offset correction, in the console 16, the ES image generation unit 61 generates an ES image and the bone density calculation unit 62 calculates bone density on the basis of the ES image. The bone density is displayed on the display 17 together with, for example, the ES image.

In a case in which the reproducibility of the X-ray image which is the origin of the calculation of the index value related to bones, such as bone density, is not ensured, there is a concern that the reliability of the index value will be significantly reduced. However, in the invention, since the reproducibility of the X-ray image is ensured, it is possible to improve the reliability of the index value.

In the configuration in which the first and second sensor panels 11A and 11B are sequentially arranged in the thickness direction, the amount of radiation reaching the second sensor panel 11B is reduced to 10% to 20% of the amount of radiation reaching the first sensor panel 11A. Therefore, the signal-noise (SN) ratio of the second X-ray image is reduced and the influence of the noise caused by a variation in ground potential on the second X-ray image is relatively large. Therefore, in a case in which the invention is applied to the configuration in which the first and second sensor panels 11A and 11B are sequentially arranged in the thickness direction, it is possible to obtain a greater effect.

Second Embodiment

Figure 7:
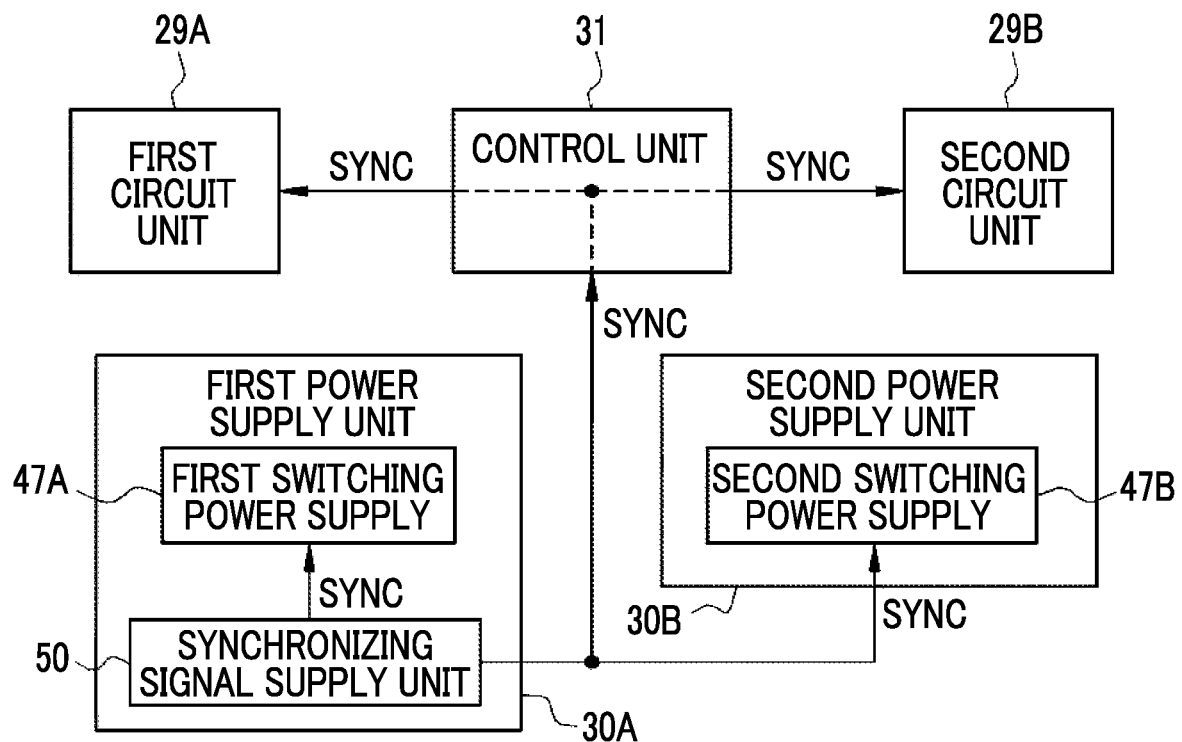
FIG. 7 is a block diagram illustrating a second embodiment in which a synchronizing signal supply unit is provided in a first power supply unit.

In a second embodiment illustrated in FIG. 7, the synchronizing signal supply unit 50 is not provided in the control unit 31, but is provided in the first power supply unit 30A. In this case, the synchronizing signal supply unit 50 supplies the synchronizing signal SYNC to the first switching power supply 47A in the first power supply unit 30A, the second switching power supply 47B in the second power supply unit 30B, and the control unit 31. The control unit 31 supplies the synchronizing signal SYNC from the synchronizing signal supply unit 50 as a clock signal to each of the first and second circuit units 29A and 29B as in the first embodiment.

Since the first switching power supply 47A is supplied with the synchronizing signal SYNC from the synchronizing signal supply unit 50 in the first power supply unit 30A to which the first switching power supply 47A belongs, the first switching power supply 47A is a so-called self-excited type. In contrast, since the second switching power supply 47B is supplied with the synchronizing signal SYNC from the synchronizing signal supply unit 50 provided in the first power supply unit 30A different from the second power supply unit 30B to which the second switching power supply 47B belongs, the second switching power supply 47B is a so-called separately excited type. In a case in which this idea is applied to the first embodiment, since each of the first and second switching power supplies 47A and 47B is supplied with the synchronizing signal SYNC from the synchronizing signal supply unit 50 in the control unit 31 in the first embodiment, each of the first and second switching power supplies 47A and 47B is a so-called separately excited type.

In addition, the synchronizing signal supply unit 50 may not be provided in the first power supply unit 30A, but may be provided in the second power supply unit 30B. That is, the synchronizing signal supply unit 50 may be provided in any one of the first and second power supply units 30A and 30B. In addition, the synchronizing signal supply unit 50 may be provided separately from the first and second power supply units 30A and 30B and the control unit 31.

Third Embodiment

Figure 8:
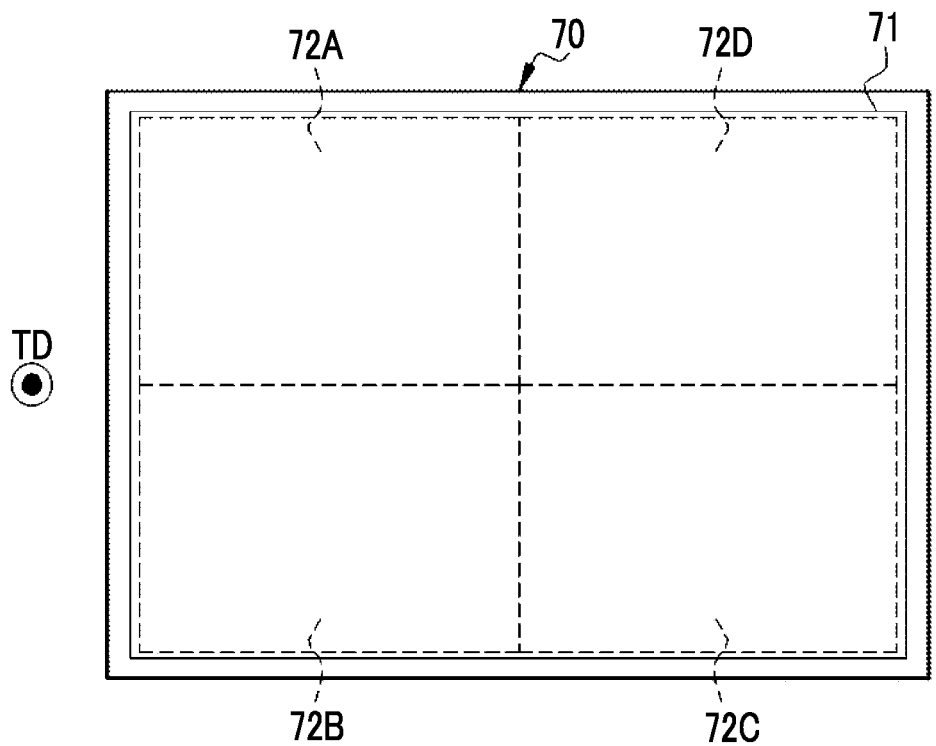
FIG. 8 is a diagram illustrating an electronic cassette according to a third embodiment as viewed from the front surface on which X-rays are incident.
Figure 9:
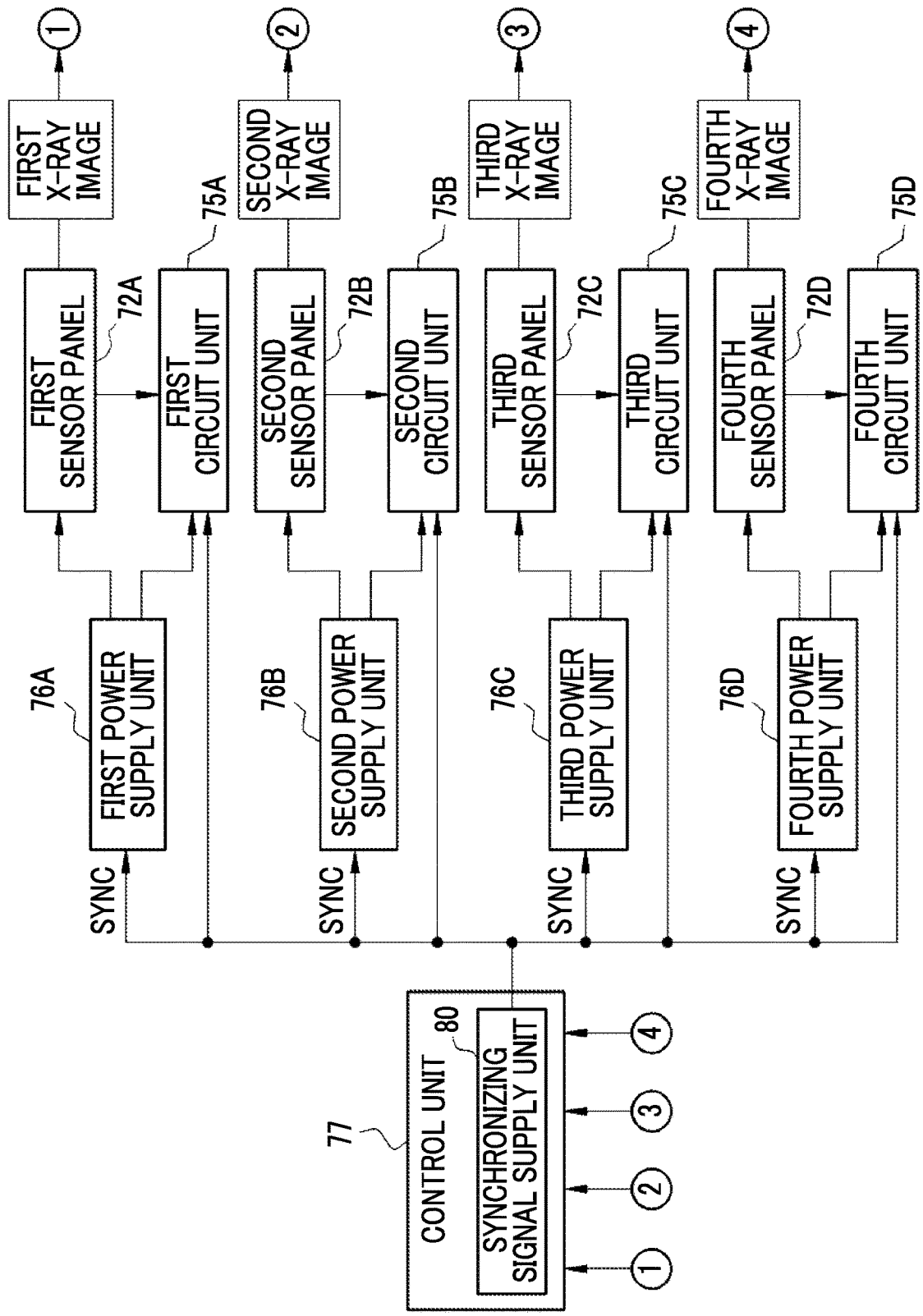
FIG. 9 is a block diagram illustrating the electrical configuration of the electronic cassette according to the third embodiment.

In a third embodiment illustrated in FIGS. 8 and 9, a plurality of sensor panels are not sequentially arranged in the thickness direction TD as illustrated in, for example, FIG. 1, but are closely arranged on the same plane perpendicular to the thickness direction TD (a direction perpendicular to the plane of paper in FIG. 8).

FIG. 8 is a diagram illustrating an electronic cassette 70 according to this embodiment as viewed from the front surface on which X-rays are incident. A transmission plate 71 that transmits X-rays is attached to an opening provided in the front surface of the electronic cassette 70 as in the electronic cassette 10 according to the first embodiment. A total of four sensor panels 72, that is, a first sensor panel 72A, a second sensor panel 72B, a third sensor panel 72C, and a fourth sensor panel 72D are closely arranged on the same plane perpendicular to the thickness direction TD.

In this case, as illustrated in FIG. 9, a first circuit unit 75A, a second circuit unit 75B, a third circuit unit 75C, and a fourth circuit unit 75D are provided in the first to fourth sensor panels 72A to 72D, respectively. In addition, a first power supply unit 76A, a second power supply unit 76B, a third power supply unit 76C, and a fourth power supply unit 76D are provided in pairs of the first to fourth sensor panels 72A to 72D and the first to fourth circuit units 75A to 75D, respectively. A synchronizing signal supply unit 80 provided in a control unit 77 supplies the synchronizing signal SYNC to each of the first to fourth circuit units 75A to 75D and each of the first to fourth power supply units 76A to 76D. In addition, the second embodiment may be applied such that the synchronizing signal supply unit 80 is provided in any one of the first to fourth power supply units 76A to 76D.

In the first to fourth sensor panels 72A to 72D, charge is accumulated in the pixels at the same time by one X-ray emission operation. A first X-ray image, a second X-ray image, a third X-ray image, and a fourth X-ray image detected from the first to fourth sensor panels 72A to 72D are transmitted to the console 16 through the control unit 77. The console 16 connects the X-ray images at positions corresponding to the arrangement of the first to fourth sensor panels 72A to 72D to generate one X-ray image and displays the X-ray image on the display 17. As such, the plurality of sensor panels may be sequentially arranged in the thickness direction as in the first embodiment or may be closely arranged on the same plane as in this embodiment.

The state in which "the plurality of sensor panels are sequentially arranged in the thickness direction" is not limited to the state in which a plurality of sensor panels are closely arranged as in each of the above-described embodiments. The state in which "the plurality of sensor panels are sequentially arranged in the thickness direction" also includes a state in which a plurality of sensor panels are not closely arranged and are separated from each other with a gap therebetween and a state in which an insert, such as an X-ray filter for restricting the incidence of soft ray components of X-rays, is interposed between a plurality of sensor panels.

In each of the above-described embodiments, the electronic cassette is given as an example of the radiographic image detection device. However, the invention is not limited thereto. The invention can also be applied to a stationary radiographic image detection device that is fixed to the imaging table. In addition, the invention is not limited to X-rays and can also be applied to a case in which other types of radiation, such as γ-rays, are used.

The conjunction "or" described in the specification is not an expression intended to be a limited interpretation of any one of a plurality of options connected by the conjunction depending on the context, but is an expression including combinations of the plurality of options. For example, a sentence "an option A or an option B is performed" needs to be interpreted as having the following three meanings, depending on the context: "an option A is performed"; "an option B is performed"; and "an option A and an option B are performed".

The invention is not limited to each of the above-described embodiments and various configurations may be used as long as they do not depart from the scope and spirit of the invention.

EXPLANATION OF REFERENCES

10, 70: electronic cassette (radiographic image detection device)
11A: first sensor panel
11B: second sensor panel
12: housing
13: imaging table
14: holder
15: X-ray source (radiation source)
16: console
17: display
18: input device
25, 71: transmission plate
26A, 26B: first and second light detection substrates
27A, 27B: first and second scintillators
28: base
29A, 29B: first and second circuit units
30A, 30B: first and second power supply units
31, 77: control unit
40A, 40B: first and second pixels
41A, 41B: first and second gate lines
42A, 42B: first and second signal lines
43A, 43B: first and second photoelectric conversion units
44A, 44B: first and second TFTs
45A, 45B: first and second gate driving circuits
46A, 46B: first and second signal processing units
47A, 47B: first and second switching power supplies
50, 80: synchronizing signal supply unit
60A, 60B: first and second offset correction units
61: ES image generation unit
62: bone density calculation unit
72A to 72D: first to fourth sensor panels
75A to 75D: first to fourth circuit units
76A to 76D: first to fourth power supply units
H: subject
TD: thickness direction
X: row direction of pixel
Y: column direction of pixel
SYNC: synchronizing signal
PA, PB: pulses of first and second switching power supplies

What is claimed is:
1. A radiographic image detection device comprising:
a plurality of sensor panels in which pixels that accumulate charge in response to radiation, which has been emitted from a radiation source and transmitted through a subject, are two-dimensionally arranged;
a plurality of circuit units each of which is provided in each of the plurality of sensor panels, converts the charge into a digital signal, and outputs the digital signal as a radiographic image;
a plurality of power supply units each of which is provided for each pair of the sensor panel and the circuit unit and supplies power to each pair of the sensor panel and the circuit unit; and a synchronizing signal supply unit that supplies a synchronizing signal for synchronizing operations of the plurality of power supply units to the plurality of power supply units.

2. The radiographic image detection device according to claim 1, further comprising:
a control unit that controls operations of the sensor panels,
wherein the synchronizing signal supply unit is provided in the control unit.

3. The radiographic image detection device according to claim 1,
wherein the synchronizing signal supply unit is provided in one of the plurality of power supply units.

4. The radiographic image detection device according to claim 1,
wherein the synchronizing signal is used as a clock signal for regulating operations of the circuit units.

5. The radiographic image detection device according to claim 1,
wherein the plurality of sensor panels are sequentially arranged in a thickness direction.

6. The radiographic image detection device according to claim 5,
wherein a plurality of the radiographic images output from the plurality of circuit units are used to calculate an index value related to bones.

* * * * *